US012687598B2

(12) United States Patent
Wang et al.

(10) Patent No.: US 12,687,598 B2
(45) Date of Patent: Jul. 21, 2026

(54) MAGNETIC RESONANCE COMPATIBLE ROBOT SYSTEM

(71) Applicant: Beijing Precision Medtech Co., Ltd., Beijing (CN)

(72) Inventors: Jia Wang, Beijing (CN); Daqing Wang, Beijing (CN)

(73) Assignee: Beijing Precision Medtech Co., Ltd., Beijing (CN)

( * ) Notice: Subject to any disclaimer, the term of this patent is extended or adjusted under 35 U.S.C. 154(b) by 287 days.

(21) Appl. No.: 18/534,771

(22) Filed: Dec. 11, 2023

(65) Prior Publication Data

US 2024/0210504 A1      Jun. 27, 2024

Related U.S. Application Data

(63) Continuation of application No. PCT/CN2022/097936, filed on Jun. 9, 2022.

(30) Foreign Application Priority Data

Jun. 11, 2021      (CN) ......................... 202110652399.1

(51) Int. Cl.
*G01R 33/421*      (2006.01)
*A61B 34/30*       (2016.01)

(52) U.S. Cl.
CPC .......... *G01R 33/4215* (2013.01); *A61B 34/30* (2016.02)

(58) Field of Classification Search
CPC .. A61B 34/30; G01R 33/4215; H05K 1/0216; H05K 1/147; H05K 1/189; H05K 9/0007;
(Continued)

(56) References Cited

U.S. PATENT DOCUMENTS

2004/0111183 A1      6/2004   Sutherland et al.
2006/0106443 A1*    5/2006   Michael ................. A61N 1/056
                                                                     607/122
(Continued)

FOREIGN PATENT DOCUMENTS

CN        108281222 Y       7/2018
CN        108882965 Y      11/2018
(Continued)

OTHER PUBLICATIONS

Y. Shi, N. Li, C. C. Tremblay and S. Martel, "A Piezoelectric Robotic System for MRI Targeting Assessments of Therapeutics During Dipole Field Navigation," in IEEE/ASME Transactions on Mechatronics, vol. 26, No. 1, pp. 214-225, Feb. 2021, doi: 10.1109/ TMECH.2020.3009829 (Year: 2020).*
(Continued)

*Primary Examiner* — Boniface N Nganga
(74) *Attorney, Agent, or Firm* — Hemisphere Law, PLLC

(57)                            ABSTRACT

The present invention provides a magnetic resonance compatible robot system, which belongs to the technical field of medical robots. The robot system comprises a robot body, a control cabinet and cables, the control cabinet is used for controlling the operation of the robot body via the cables, and the robot body comprises motors and encoders, each of which is externally provided with an insulation film, a metal shielding layer and an insulation shell in sequence. The processing scheme of the present disclosure can improve the compatibility of the robot system with the MRI system and greatly reduce noise and artifacts on MRI images, so as to realize real-time image-guided interventional surgery.

10 Claims, 7 Drawing Sheets

(58) Field of Classification Search

CPC ...... H01B 7/041; H02K 11/0141; B25J 11/00; B25J 19/0075

See application file for complete search history.

(56) References Cited

U.S. PATENT DOCUMENTS

| 2008/0024213 A1* | 1/2008 | Magrath | ................... | H03F 3/68 |
| | | | | 330/96 |
| 2011/0197553 A1* | 8/2011 | Su | ........................... | B65B 27/06 |
| | | | | 53/588 |
| 2017/0290630 A1* | 10/2017 | Goldenberg | ......... | A61B 5/0046 |
| 2021/0159764 A1 | 5/2021 | Nimura et al. | | |

FOREIGN PATENT DOCUMENTS

| CN | 112587121 Y | 4/2021 |
| CN | 113400322 | 9/2021 |

OTHER PUBLICATIONS

N. A. Patel et al., "An Integrated Robotic System for MRI-Guided Neuroablation: Preclinical Evaluation," in IEEE Transactions on Biomedical Engineering, vol. 67, No. 10, pp. 2990-2999, Oct. 2020, doi: 10.1109/TBME.2020.2974583 (Year: 2020).*

International search report of PCT/CN2022/097936.

* cited by examiner

| Test Mode | Signal intensity (A) | Noise intensity Sdev(B) | SNR(A/B) | SNR change |
|---|---|---|---|---|
| 1a. Reference point without electrical shielding | | | | |
| Water phantom noise (Area 3000 mm^2) | 1481 | 8.64 | 171 | |
| Device not connected and placed above water phantom | 1449.867 | 9.136 | 189 | -7% |
| 1b. Test results without electrical shielding | | | | |
| Device connected but not energized | 1713 | 29.2 | 59 | -66% |
| Energized but not running | 1547.5 | 55.1 | 28 | -84% |
| Energized and running | 1571.7 | 70.5 | 22 | -87% |
| 2a. Reference point after electrical shielding | | | | |
| Water phantom noise (Area 3000 mm^2) | 1.342.67 | 7.765 | 173 | |
| Device not connected and placed above water phantom | 1105.462 | 7.212 | 153 | -11% |
| 2b. Test results after electrical shielding | | | | |
| Device connected but not energized | 1080.903 | 7.078 | 153 | -12% |
| Energized but not running | 1085.707 | 7.173 | 151 | -12% |
| Energized and running | 1046.427 | 6.971 | 150 | -13% |

FIG.6

MAGNETIC RESONANCE COMPATIBLE ROBOT SYSTEM

TECHNICAL FIELD

The present disclosure relates to the technical field of medical robots, and relates to a magnetic resonance compatible robot system, in particular to a circuit shielding protection system for a robot system in magnetic resonance environments.

BACKGROUND

Architectural magnetic resonance imaging (MRI) has excellent soft tissue contrast and spatial resolution in any direction, and has less radiation hazards than computed tomography (CT). In addition, MRI images can be used to examine texture characteristic in the body and observe positions of surgical instruments in the body. With regard to liver cancer, for example, MRI can identify lesions less than 20 mm in diameter, while ultrasonography and CT are difficult to locate such small lesions. MRI-guided minimally invasive robotic surgery has become a more and more extensive application and urgent need.

However, interventional surgical robot products suitable for MRI environments are very limited in the market at present. The reason for this is multiple challenges of developing MRI-guided surgical robots. For example, the requirements for MRI bidirectional compatibility are as follows: on one hand, the electrical system of the robot shall not interfere with MRI scanning functions nor cause image artifacts; and on the other hand, the magnetic field, the gradient field and the radio-frequency (RF) field of the MRI device shall not interfere with the normal use of the electrical system of the robot. For another example, the space limitation of MRI scanning holes is a great challenge for the electrical design of surgical robots. To meet the requirements for MRI compatibility, the layout of electronic components and the electrical shielding measures need to be considered.

In the patent document U.S. Pat. No. 8,275,443 B2, the robot and the sequential scanning cannot run simultaneously: once the motor is energized, the quality of MRI images declines, noise and artifacts appear. If the motor is running, the quality of MRI images will continue to decline. The reason is that although the ultrasonic motor is suitable for MRI environments, the drive electronics that control the operation of the motor often produce noise on the MRI images. Typically, the drive electronics of the motor will produce RF noise when energized. In addition, long cables for motor drive and communication can serve as antennas for transmitting RF signals that interfere with the MR imaging process. Such interference comes in a form of noise and artifacts on MRI images. This is a typical problem that impedes simultaneous operation of the ultrasonic motor and MRI scanning. A widely accepted solution is to run the motor when sequential scanning is stopped, and vice versa. However, this method cannot achieve real-time interventional surgery.

SUMMARY

In view of this, embodiments of the present disclosure provide a magnetic resonance compatible robot system, which at least partially solves the problems in the prior art. The magnetic resonance compatible robot system provided by the present invention comprises a robot body, a control cabinet and cables, the control cabinet is used for controlling the operation of the robot body via the cables, and the robot body comprises motors and encoders, each of which is externally provided with an insulation film, a metal shielding layer and an insulation shell in sequence.

In one specific embodiment according to embodiments of the present invention, the insulation film is insulating coating covering the outside of the motor and the encoder, and the metal shielding layer is a metal shielding film covering the inside of the insulation shell.

In one specific embodiment according to embodiments of the present invention, the cables comprise an encoder shielding cable and a motor drive shielding cable located in the robot body, and the encoder shielding cable and the motor drive shielding cable are both made by a flexible printed circuit board technology.

In one specific embodiment according to embodiments of the present invention, the cables comprise communication cables for communication and motor drive cables for motor drive, the encoder shielding cable is connected with the communication cables via an encoder jumper holder, and the motor drive shielding cable is connected with the motor drive cables via a motor drive cable jumper holder.

In one specific embodiment according to embodiments of the present invention, the motor drive shielding cable is integrated with a harmonic filter on one end of the motor drive cable jumper holder for adjusting electrical performance of the motor.

In one specific embodiment according to embodiments of the present invention, the communication cables and the motor drive cables for motor drive are connected to the control cabinet respectively via low pass filters, a special grounding body and a shielding wall, and the low pass filters are arranged in the shielding wall.

In one specific embodiment according to embodiments of the present invention, the motor drive cables each comprise a wire, a wire insulation layer arranged outside the wire, an inner shielding layer covering the wire insulation layer, an outer shielding layer arranged outside the inner shielding layer and an outer insulation layer arranged outside the outer shielding layer from inside to outside in sequence.

In one specific embodiment according to embodiments of the present invention, the communication cables each comprise a twisted pair, an inner shielding layer arranged outside the twisted pair, an outer shielding layer arranged outside the inner shielding layer and an outer insulation layer arranged outside the outer shielding layer from inside to outside in sequence, wherein each wire of the twisted pair is externally provided with a wire insulation layer. The two layers of shielding constitute a double shielding layer.

In one specific embodiment according to embodiments of the present invention, the inner shielding layer and the double shielding layer are double shielding layers of metal foil and metal braid wire mesh.

In one specific embodiment according to embodiments of the present invention, the outer shielding layer, the inner shielding layer and the double shielding layer are connected with the special grounding body.

In one specific embodiment according to embodiments of the present invention, housings of the low pass filters are made of metal with favorable conductivity and are connected with the special grounding body. In one specific embodiment according to embodiments of the present invention, the control cabinet has an aluminum housing, and the aluminum housing is connected to a protective grounding body.

In one specific embodiment according to embodiments of the present invention, the robot system also comprises a driver, the driver is used for driving the motor, the driver comprises a controller and a linear power amplification circuit, the controller is used for producing drive signals, and the linear power amplification circuit performs linear power amplification of the drive signals.

In one specific embodiment according to embodiments of the present invention, the linear power amplification circuit comprises biasing circuits and amplifying circuits, each biasing circuit is used for isolating DC voltage components of each amplifying circuit and providing bias voltage for the amplifying circuit, and the amplifying circuit is used for amplifying the drive signals.

The magnetic resonance compatible robot system in the embodiments of the present disclosure comprises a robot body, a control cabinet and cables, the control cabinet is used for controlling the operation of the robot body via the cables, and the robot body comprises motors and encoders, each of which is externally provided with an insulation film, a metal shielding layer and an insulation shell in sequence. The processing scheme of the present disclosure can improve the compatibility of the robot system with the MRI system and greatly reduce noise and artifacts on MRI images, so as to realize real-time image-guided interventional surgery.

DESCRIPTION OF DRAWINGS

To more clearly describe the technical solutions in embodiments of the present disclosure, the drawings required to be used in the embodiments will be simply presented below. Apparently, the drawings in the following description are merely some embodiments of the present disclosure, and for those skilled in the art, other drawings can also be obtained according to these drawings without contributing creative labor.

FIG. 6 is a schematic diagram of a data sheet of an electrical performance test;

Figure 1:
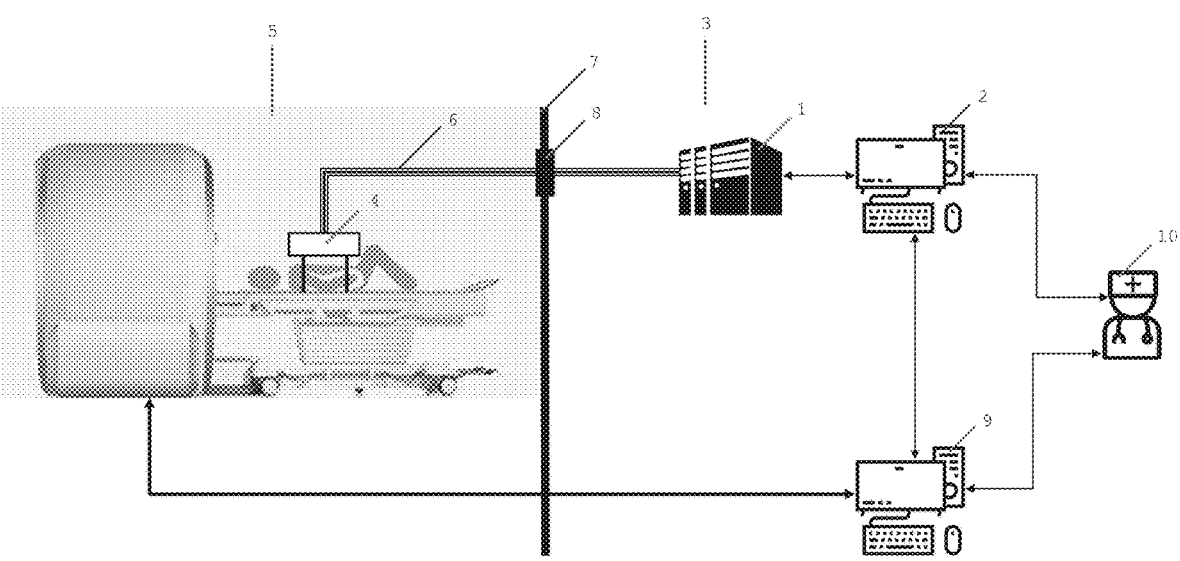
FIG. 1 shows a system architecture and a working environment of a robot system in embodiments of the present invention.

In the figures, 1—control cabinet, 2—workstation, 3—MRI control room, 4—robot body, 5—MRI scanning room, 6—cable, 7—shielding wall, 8—filter, 9—MRI workstation, 10—doctor, 11—motor, 12—encoder, 13—motor driver, 14—special grounding body, 15/16—communication cable, 17/18—motor drive cable, 19/20—filter, 21—encoder jumper holder, 22—motor drive cable jumper holder, 23—interface board, 24—outer insulation layer, 25—outer shielding layer, 26—motor drive cable inner shielding layer, 27—wire, 28—wire insulation layer, 29—twisted pair, 30—insulation film, 31—insulation shell, 32—metal shielding layer, 33—cable connector housing, 34—encoder shielding cable, 35—motor drive shielding cable, 36—harmonic filter, 37—protective grounding body, 38—controller, 39—biasing circuit, 40—amplifying circuit, and 41—communication cable inner shielding layer.

DETAILED DESCRIPTION

Embodiments of the present disclosure will be described below in detail in combination with drawings.

Embodiments of the present disclosure are described below through specific embodiments. Those skilled in the art can understand other advantages and effects of the present disclosure easily through the disclosure of the description. Apparently, the described embodiments are merely part of the embodiments of the present disclosure, not all of the embodiments. The present disclosure can also be implemented or applied through additional different specific embodiments. All details in the description can be modified or changed based on different perspectives and applications without departing from the spirit of the present disclosure. It should be explained that if there is no conflict, the following embodiments and the features in the embodiments can be mutually combined. Based on the embodiments in the present disclosure, all other embodiments obtained by those skilled in the art without contributing creative labor will belong to the protection scope of the present disclosure.

It should be indicated that various aspects of the embodiments within the scope of the attached claims are described below. It should be obvious that the aspects described herein can be reflected in a wide variety of forms and any particular structure and/or function described herein is illustrative only. Based on the present disclosure, those skilled in the art should understand that one aspect described herein can be implemented independently of any other aspect and two or more of these aspects can be combined in various ways. For example, a device and/or a method can be implemented using any number of aspects described herein. In addition, the device and/or the method can be implemented using structures and/or functionality other than one or more of the aspects described herein.

It should also be indicated that the figures provided in the following embodiments only exemplarily explain the basic conception of the present disclosure, so only show the components associated with the present disclosure, and are not drawn in accordance with component number, shapes and sizes in actual implementation. Forms, number and proportions of the components in the actual implementation can be freely changed, and component layout forms may also be more complex.

In addition, specific details are provided in the following description to facilitate a thorough understanding of the embodiments. However, those skilled in the art will understand that the aspects can be practiced without these specific details.

The magnetic resonance compatible robot system proposed by the present invention can meet the magnetic resonance compatibility of the electrical system, realize simultaneous operation of the robot system and MRI scanning, and effectively reduce the noise and artifacts on MRI images during the operation of the system, so as to realize real-time image-guided interventional surgery.

Next, the magnetic resonance compatible robot system of the present invention is described in detail with reference to the drawings.

Overall Arrangement:

First of all, the system architecture and the working environment of the robot system in embodiments of the present invention are described with reference to FIG. 1. The robot system according to the present invention comprises a control cabinet 1, a workstation 2, a robot body 4, cables 6 and a filter 8, wherein the workstation 2 is in communicating connection with the control cabinet 1, and the control cabinet 1 is connected with the robot body 4 via the filter 8 through the cables 6 to control the operation of the robot body 4.

In addition, the robot system of the present invention can be matched with the MRI system to realize MRI system-guided robot surgery, wherein the MRI system can be a conventional MRI system, and can comprise an MRI device and an MRI workstation 9.

In the present invention, the workstation 2 is an operating console of the robot system, which can be implemented in the form of one or more navigation planning computers with a user interaction interface. The workstation 2 is connected with the control cabinet 1 and the MRI workstation 9 respectively. At work, an operator such as a surgeon 10 issues a command to the workstation 2 through the user interaction interface of the workstation 2, the workstation 2 transmits the command to the control cabinet 1, and the control cabinet 1 provides power and the control command to the robot body 4 via the cables 6 so that the surgical robot 4 executes the command. It should be understood that the robot system and the MRI system can also comprise other components not shown in the present invention.

Figure 2:
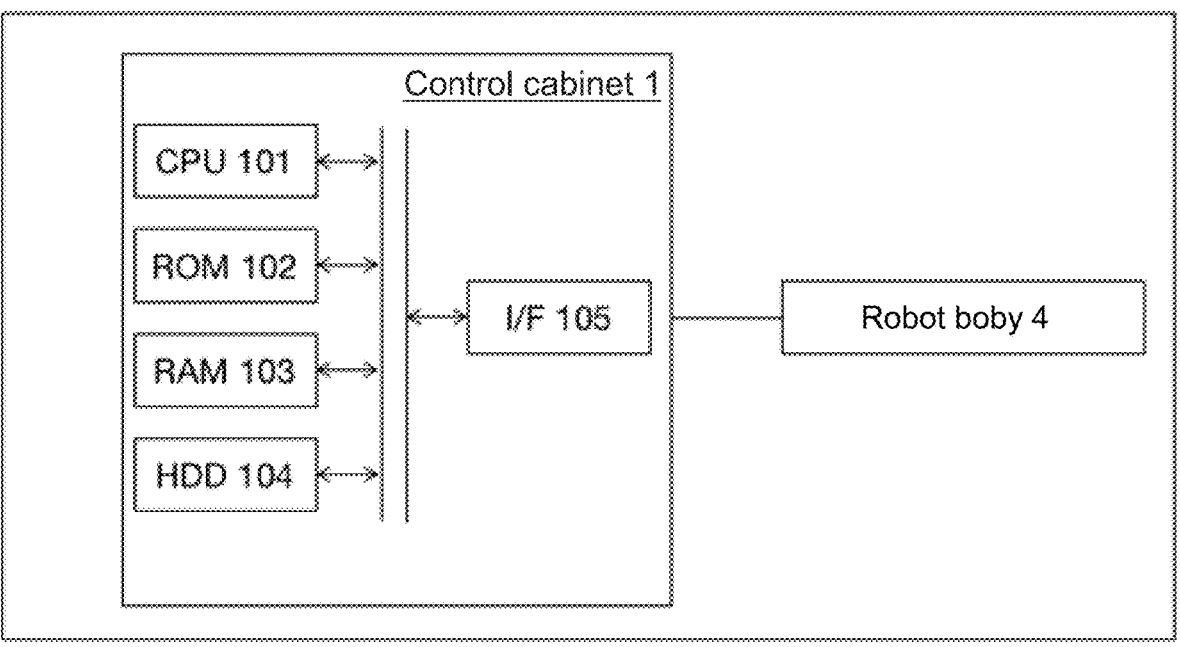
FIG. 2 is a structural schematic diagram of a control cabinet in embodiments of the present invention.

FIG. 2 is a structural schematic diagram of the control cabinet 1 of the present invention. The control cabinet 1 comprises a central processing unit (CPU) 101 as a control unit. In addition, the control cabinet 1 comprises a read-only memory (ROM) 102, a random access memory (RAM) 103 and a hard disk drive (HDD) 104. In addition, the control cabinet 1 comprises an interface I/F 105. ROM 102, RAM 103, HDD 104 and I/F 105 are connected to CPU 101 via buses. Basic programs used to make CPU 101 run are stored in ROM 102. RAM 103 is a storage device in which various data such as computing results of CPU 101 are temporarily stored. HDD 104 is a storage device in which computing results of CPU 101 are stored and programs used to make CPU 101 execute various controls are recorded. CPU 101 is used for controlling the operation of the robot body 4 according to the programs recorded in HDD 104.

In the present invention, to reduce the impact of the strong magnetic field of the MRI device on the electronic devices (such as MRI workstation 9) of the MRI device and the electronic devices (such as motor driver 13) of the robot system, the MRI device is placed in the MRI scanning room 5, the MRI workstation 9 is placed in the MRI control room 3, and the MRI scanning room 5 and MRI control room 3 can be isolated, for example, by the shielding wall 7, thus reducing the impact of the strong magnetic field in the MRI scanning room 5 on the electronic devices in the MRI control room 3. That is to say, the MRI device is arranged separately from the control device thereof.

Moreover, in order to effectively reduce electromagnetic interference caused by the electronic devices of the robot system and interference of RF signals to the MRI system, the control cabinet 1 and the workstation 2 of the robot system of the present invention are placed in the MRI control room 3, and the robot body 4 driven by the ultrasonic motor is placed in the MRI scanning room 5. That is to say, the control cabinet 1, the workstation 2 and the MRI workstation 9 are placed in the MRI control room 3, the robot body 4 and the MRI device are placed in the MRI scanning room 5, and the control cabinet 1 and the robot body 4 are connected through the shielded cable 6 so that the electromagnetic interference and the RF signal interference can be reduced by minimizing the electronic devices in the MRI scanning room 5.

In the present invention, the main electrical components of the robot body 4 comprise motors 11 and encoders 12, the main electrical components of the control cabinet 1 comprise motor drivers 13, and the cables 6 can comprise communication cables for communication and motor drive cables for motor drive. The control cabinet 1 and the robot body 4 are connected through the shielded cable 6, the cable 6 passes through the shielding wall 7 between the MRI scanning room 5 and the MRI control room 3 via the filter 8, and the filter 8 can be embedded in the shielding wall 7. Therefore, the utilization rate of space is increased, and the electromagnetic interference and the RF signal interference are minimized. More specifically, the compatibility of the robot system with the MRI system can be improved by arranging the components of the robot system in this way.

In the present invention, the motor 11 can be an ultrasonic motor and also can be another type of electromagnetic compatible motor, and the encoder 12 can be a general-purpose encoder.

Moreover, the robot system of the present invention combines shielding, grounding and filtering so that the noise and artifacts on the MRI images can be greatly reduced when the ultrasonic motor is used. These features of the robot system of the present invention are further described below in combination with the drawings.

Figure 3:
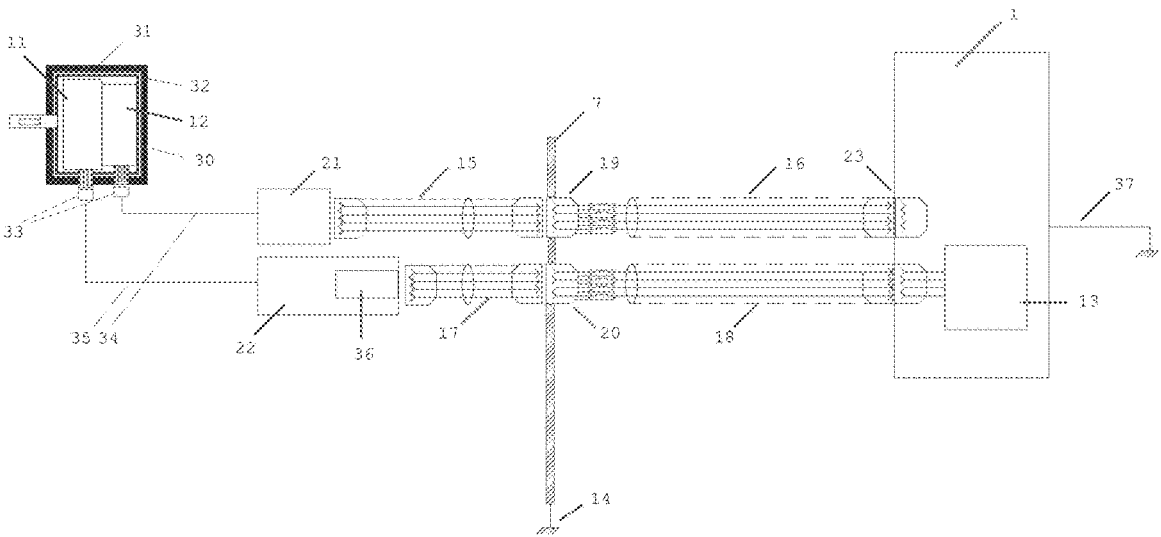
FIG. 3 is a schematic diagram of shielding and grounding of an electrical system of a robot system in embodiments of the present invention.

Arrangement of Motor and Encoder:

FIG. 3 is a schematic diagram of shielding and grounding of the electrical system of the robot system of the present invention. In the present invention, the main electrical components of the robot body 4 comprise motors 11 and encoders 12, the main electrical components of the control cabinet 1 comprise motor drivers 13, and the cables 6 can comprise communication cables 15/16 for communication and motor drive cables 17/18 for motor drive.

Since the motors 11 and the encoders 12 are arranged in the MRI scanning chamber 5, the electromagnetic compatibility and insulation thereof are important for improving the quality of the MRI images and the safety of operators.

In the present invention, the motor 11 and the encoder 12 of the robot body 4 are MRI-compatible and do not contain ferromagnetic materials. At least one insulation film 30 is arranged outside the motor 11 and the encoder 12 to improve the insulation level and safety protection level of the motor 11 and the encoder 12. The insulating film 30 can be, for example, insulating coating, and be covered on the outside of boxes of the motor 11 and the encoder 12.

In addition, to prevent bidirectional RF signal interference between the motor 11 and the encoder 12 and the MRI device, a Faraday cage or a metal shielding layer 32 is also required to be arranged outside the motor 11 and the encoder 12. The metal shielding layer 32 needs to be connected with a cable shielding layer described subsequently as well as an encoder shielding cable 34 and a cable connector housing 33 of a motor drive shielding cable 35.

Moreover, an insulation shell 31 is also required to be arranged outside the metal shielding layer 32 to meet the requirements of the insulation level and safety protection level.

That is to say, in the present invention, the motor 11 and the encoder 12 are externally provided with the insulation film 30, the metal shielding layer 32 and the insulation shell 31, so as to realize the requirements of shielding, insulation and safety protection.

Since the robot system needs to adapt to small space in the MRI device, the electrical components also need a relatively compact design. Therefore, the metal shielding layer 32 of the present invention is not a single shielding shell, but a metal shielding film covering the inside of the insulation shell 31, and the metal shielding film can be metal plating, for example, and also can be metal coating. In addition, the insulating film 30 can be insulating coating covering the outside of the boxes of the motor 11 and the encoder 12. The compact shielding insulation design of the present invention can effectively solve the problem of bidirectional compatibility between the motor 11 and the encoder 12 and the MRI device in narrow space.

Arrangement of Cable:

In the present invention, the cables 6 comprise a plurality of parts, and the cables located in the robot body 4 comprise an encoder shielding cable 34 and a motor drive shielding cable 35, wherein the encoder shielding cable 34 is used for the communication of the encoder and the motor drive shielding cable 35 is used for the drive of the motor 11. Both the encoder shielding cable 34 and the motor drive shielding cable 35 can be made by the flexible printed circuit board technology, with one end connected to the motor 11 and the encoder 12 respectively via the cable connector housing 33 and the other end connected to the motor drive cable jumper holder 22 and the encoder jumper holder 21 respectively. The motor drive cable jumper holder 22 and the encoder jumper holder 21 combine the motor drive wire and the encoder signal wire of each joint to reduce the number of cables connected to the control cabinet by combining the same signal wires and provide a mechanical fixing method for connectors.

In the present invention, the motor drive shielding cable 35 is integrated with a harmonic filter 36 on one end of the motor drive cable jumper holder 22 for adjusting electrical performance of the motor 11 by filtering.

In the present invention, the encoder shielding cable 34 and the motor drive shielding cable 35 used for controlling the joints of the robot body 4 are designed and arranged in the robot body 4 by the flexible printed circuit board technology, so as to adapt to narrow and limited space in the MRI device and the robot body 4. Such circuit has good shielding effect, light weight, thin thickness, small volume and good flexibility, can be easily bent and folded, is convenient for installation, and can be perfectly integrated with the structure of the robot body 4. Moreover, the circuit can also achieve dynamic bending in the moving part of the robot body 4, so as to release the constraint of the encoder shielding cable 34 and the motor drive shielding cable 35 on the motion range of the robot body 4.

In the present invention, the cables 6 also comprise communication cables 15/16 for communication and motor drive cables 17/18 for motor drive, the encoder shielding cable 34 in the robot body 4 is connected with the communication cables 15/16 via the encoder jumper holder 21, and the motor drive shielding cable 35 is connected with the motor drive cables 17/18 via the motor drive cable jumper holder 22. In the present invention, the motor drive cables 17/18 of the motor 11 and the communication cables 15/16 of the encoder 12 are both double shielded and connected to the control cabinet 1 via the low pass filters 19/20, the special grounding body 14 and the shielding wall 7. The use of the special grounding body 14 can achieve a better shielding effect than the protective grounding body, because the protective grounding body is usually connected to the ground through a long grounding cable, and other devices are also grounded through the protective grounding body.

Therefore, the protective grounding body is not considered as "clean" grounding. The special grounding body 14 is connected to the shielding wall 7, and the shielding wall 7 is used for shielding RF noise, so as to provide more reliable and "cleaner" grounding than the protective grounding body.

In the present invention, the two filters 19/20 are located between the communication cables 15/16 and the motor drive cables 17/18 respectively. The communication cable 15 is used for connecting all encoders, including position/speed encoder, zero sensor, limit sensor and force sensor, from the encoder jumper holder 21 to the input end of the filter 19. The communication cable 16 is used for connecting the output end of the filter 19 to an interface board 23 in the control cabinet 1. The motor drive cable 18 is used for connecting all drive outputs of the motor driver 13 in the control cabinet 1 to the input end of the filter 20. The motor drive cable 17 is used for connecting motor power connections of all the motors 11 from the output end of the filter 20 to the motor drive cable jumper holder 22 and from the motor drive cable jumper holder 22 to the motor 11 of each joint of the robot body 4 respectively.

Figure 4:
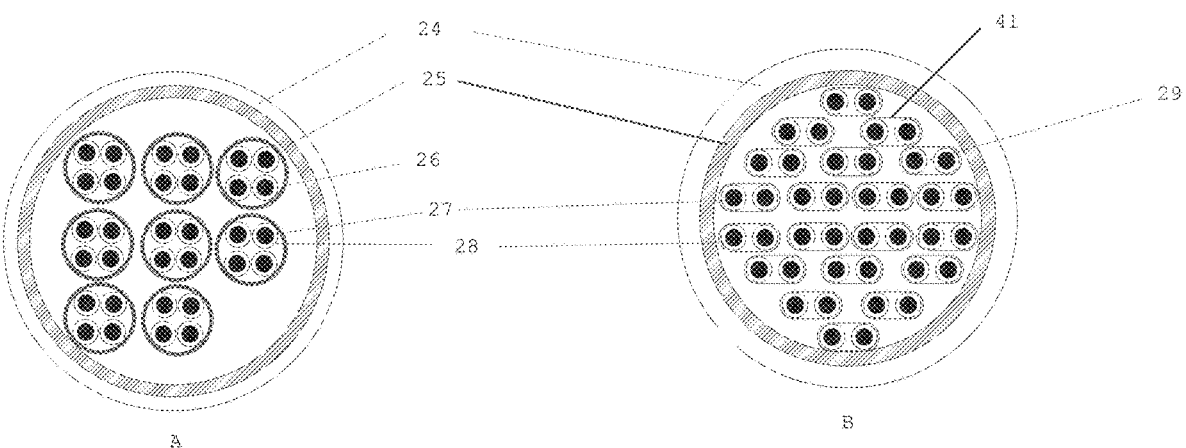
FIG. 4A is a sectional view of a motor drive cable in embodiments of the present invention.
FIG. 4B is a sectional view of a communication cable in embodiments of the present invention.

Next, the shielding of the communication cables 15/16 and the motor drive cables 17/18 is described with reference to FIG. 4A and FIG. 4B, wherein FIG. 4A shows the cross section of the motor drive cables 17/18, and FIG. 4B shows the cross section of the communication cables 15/16.

As shown in FIG. 4A, the motor drive cables 17/18 comprise a plurality of individually shielded cables, each of which is used for supplying power to one motor 11. The outer insulation layer 24 is located on the outermost part of the motor drive cables 17/18, an outer shielding braid layer, i.e., the outer shielding layer 25, is located inside the outer insulation layer 24, and the outer shielding braid layer can be, for example, tinned copper tube sleeve. In the present invention, each cable 6 is individually shielded, that is the motor drive cable inner shielding layer 26. That is to say, a separate motor drive cable inner shielding layer 26 is arranged for the cable 6 of each motor 11. In FIG. 4A, each motor 11 is provided with four cables for driving the motor 11.

In the present invention, the motor drive cable inner shielding layer 26 is a double shielding layer of metal foil and metal braid wire mesh, and more specifically, can be a double shielding layer of aluminum foil and tinned copper braid wire mesh. The double shielding layer of metal foil and metal braid wire mesh can be 100% covered on the wire insulation layer 28 outside the wire 27, thus providing better RF noise shielding than single shielding. In other words, in the present invention, the motor drive cables 17/18 each comprise a wire 27, a wire insulation layer 28 arranged outside the wire 27, a motor drive cable inner shielding layer 26 covering the wire insulation layer 28, an outer shielding layer 25 arranged outside the motor drive cable inner shielding layer 26 and an outer insulation layer 24 arranged outside the outer shielding layer 25 from inside to outside in sequence.

Moreover, in the present invention, the outer shielding layer 25 and the motor drive cable inner shielding layer 26 are connected with the special grounding body 14 of the shielding wall 7 for shielding RF noise, which is more reliable and "cleaner" than the protective grounding body.

Similar to the motor drive cables 17/18, the outer insulation layer 24 is located on the outermost part of the communication cables 15/16, an outer shielding braid layer, i.e., the outer shielding layer 25, is located inside the outer insulation layer 24, and the outer shielding braid layer 25 can be, for example, metal braid wire mesh. A communication cable inner shielding layer 41 with metal foil shielding is located inside the outer shielding braid layer 25.

In the present invention, the metal foil in the shielding material can be aluminum foil, and the metal braid wire mesh can be tinned copper braid layer. The shielding material used must have favorable conductivity. Aluminum foil with tinned copper is chosen due to a good balance thereof between shielding effect and cost. Those skilled in the art will understand that alternative RF shielding materials can also be used and other options can be bare copper, silver or gold.

In the present invention, a twisted pair 29 is arranged in the communication cable inner shielding layer 41. The twisted pair is a cable formed by twisting two wires 27 with an insulating layer 28 together. Such arrangement of the communication cables 15/16 can allow electric waves radiated by each wire during transmission to be offset by electric waves emitted by another cable, which can effectively reduce the degree of external signal interference. In other words, in the present invention, the communication cables 15/16 each comprise a twisted pair, a communication cable inner shielding layer 41 arranged outside the twisted pair, an outer shielding layer 25 arranged outside the communication cable inner shielding layer 41 and an outer insulation layer 24 arranged outside the outer shielding layer 25 from inside to outside in sequence, wherein each wire 27 in the twisted pair is externally provided with a wire insulation layer.

In the present invention, the outer shielding layer 25, the motor drive cable inner shielding layer 26 and the communication cable inner shielding layer 41 are connected with the special grounding body 14 of the shielding wall 7 for shielding RF noise, which is more reliable and "cleaner" than the protective grounding body.

It can be seen from the above description that the main difference between the communication cables 15/16 and the motor drive cables 17/18 is the existence state of the wire 27 as well as the motor drive cable inner shielding layer 26 and the communication cable inner shielding layer 41.

Specifically, the wire 27 in the communication cables 15/16 exists in a form of twisted pair to reduce signal interference during communication. Differently, the wire 27 in the motor drive cables 17/18 exists in a form of single wire 27, this is because signals transmitted by the motor drive cables 17/18 outputting power are single-ended unbalanced drive signals, while signals transmitted by the communication cables 15/16 are differential balanced signals.

In addition, the motor drive cable inner shielding layer 26 is a double shielding layer of metal foil and metal braid wire mesh, and the communication cable inner shielding layer 41 is metal foil. The reason for arranging the motor drive cable inner shielding layer 26 and the communication cable inner shielding layer 41 is that the motor drive cables 17/18 transmit high-voltage, high-frequency and relatively large current signals and the electromagnetic interference to magnetic resonance images is mainly caused by the motor drive cables 17/18, so the shielding requirements are higher. Therefore, the motor drive cable inner shielding layer 26 is double shielded, and the outer shielding layer 25 is stilled needed. Different from the motor drive cables 17/18, the communication cables 15/16 mainly transmit low-voltage, low-frequency and small current signals, which has small influence on magnetic resonance images, so shielding is not required to meet the high requirements of the motor drive cables 17/18, so as to save cost.

Arrangement of Control Cabinet:

In the present invention, the control cabinet 1 has an aluminum housing, all control electronic components are located in the aluminum housing, and the aluminum housing of the control cabinet 1 is connected to the protective grounding body 37. The control cabinet 1 is simultaneously shielded and grounded by the aluminum housing, which can effectively shield RF noise.

Arrangement of Driver:

In the present invention, the motor driver 13 is used for controlling the operation of the motor 11, and the motor drive power is transferred to the motor 11 through the motor drive cable 18, the filter 20 and the motor drive cable 17.

Figure 5:
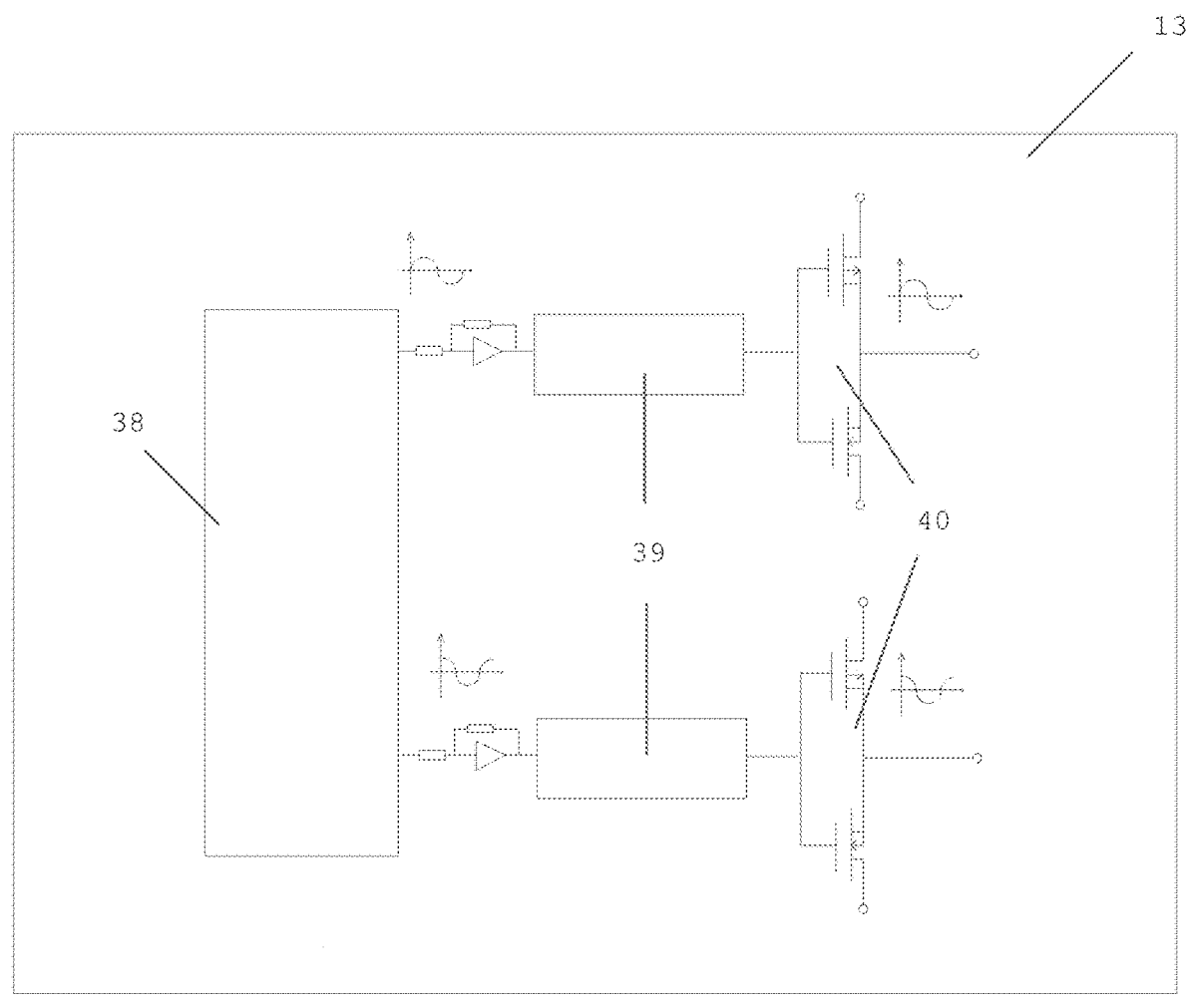
FIG. 5 is a schematic circuit diagram of a motor driver

FIG. 5 is a schematic circuit diagram of the motor driver 13. The motor driver 13 of the present invention adopts a linear drive technology and comprises a controller 38, a biasing circuit 39 and an amplifying circuit 40, and the controller 38 contains a high-performance microprocessor to produce traveling waves, so as to provide optimal drive signals for the motor 11 and drive the motor 11 after linear power amplification. The controller 38 controls the speed of the motor 11 by converting the frequency of the traveling waves. The linear power amplification circuit is used for linear power amplification and comprises a biasing circuit 39 and an amplifying circuit 40, the amplifying circuit 40 is used for amplifying drive signals to +/−200 V or 400 V peak voltage, and the biasing circuit 39 is used for isolating DC voltage components of each amplifying circuit 40 and providing bias voltage required for normal operation of the amplifying circuit 40 to make the amplifying circuit 40 work normally.

At present, the existing motor drivers 13 in the market usually adopts a switching mode to produce square signals to drive the ultrasonic motor 11, because the switching mode can obtain higher efficiency, low driver heat, small size and low cost. However, the square signals produced by the switching mode usually contain more high-order harmonics, and the high-order harmonics will produce higher electromagnetic interference during transmission, which will cause impacts such as shadow, bright spots and image deformation on MRI images.

Differently, the linear drive technology adopted in the present invention produces single-frequency pure sine waves with less high-frequency harmonic components, which can reduce interference to MRI images. Moreover, since the optimal driving mode of the traveling wave ultrasonic motor is sine wave drive of two phases with a difference of 90°, the sine wave produced by the linear driver is a drive signal most suitable for the ultrasonic motor. Therefore, the motor driver will be modified in the present invention to produce purer sine waves for driving the motor and reduce the impact of the electrical system on MRI imaging, so as to meet the requirement that the robot and MRI scanning can be carried out in real time.

Arrangement of Filter

The MRI device is usually sensitive to signals in a specific frequency range. For example, a 3.0 T MR scanner operates at a frequency of 127.8 MHz and is sensitive to RF signals near the frequency. In the present invention, noise at this frequency and higher frequencies is reduced by arranging the low pass filters 19 and 20. "Low pass" filters mean that only low-frequency signals can pass through, while high-frequency signals will be filtered out. Filtering parameters will depend on magnetic field strength, Larmor frequency, motor parameters, cable parameters, signal frequency and bandwidth, signal power, working voltage and current, and load impedance. In the present invention, the housing of the filter is connected with the special grounding body 14. The comprehensive grounding, shielding and filtering technology can effectively reduce RF noise and eliminate interference and artifacts to make the system and MR scanning run simultaneously.

Electrical Performance Test of Robot System

Figure 7:
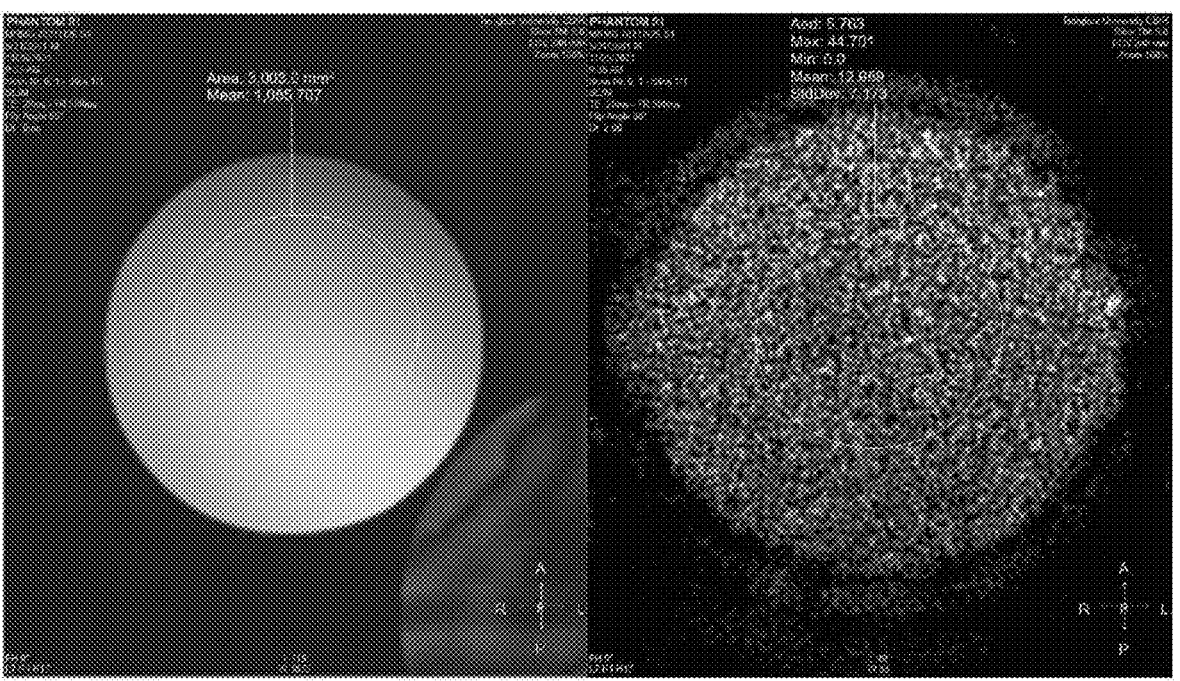
FIG. 7 is a schematic diagram of signal and noise measurement values of water phantom under magnetic resonance scanning.

FIG. 6 shows different test modes and corresponding signal intensities, noise intensities, signal-to-noise ratios (SNRs) and SNR percentage changes. The electrical performance is tested in a Philips 3.0 T magnetic resonance cavity. In the SNR test, the ratio of the signal intensity to the noise of water phantom under scanning is taken as a reference point, and the SNR percentage change is obtained by modifying the test mode. The smaller the SNR percentage change is, the more effective the shielding is. In contrast, the SNR change without electrical shielding can reach a maximum of −87%, and after patented electrical treatment, the maximum SNR change is only −13%. FIG. 7 is a schematic diagram of signal and noise measurement values of water phantom under magnetic resonance scanning, wherein the left part shows the area and the signal intensity in sequence from top to bottom, and the right part shows the noise intensity and the noise intensity standard deviation in sequence from top to bottom.

The robot system of the present invention can improve the compatibility of the robot system with the MRI system by the arrangement of the insulation film, the metal shielding layer and the insulation shell in sequence outside the motor and the encoder and the integrate design of shielding, filtering and grounding, thus greatly reducing noise and artifacts on MRI images.

The above only describes specific embodiments of the present disclosure, but the protection scope of the present disclosure is not limited thereto. Any change or replacement contemplated easily by those skilled in the art familiar with the technical field within the technical scope disclosed by the present disclosure shall be covered within the protection scope of the present disclosure. Therefore, the protection scope of the present disclosure should be determined by the protection scope of the claims.

What is claimed is:

1. A magnetic resonance compatible robot system, comprising a robot body (4), a control cabinet (1) and cables (6), the control cabinet (1) is used for controlling the operation of the robot body (4) via the cables (6), wherein the robot body (4) comprises motors (11) and encoders (12), each of which is externally provided with an insulation film (30), a metal shielding layer (32) and an insulation shell (31) in sequence, and the cables (6) comprise communication cables (15, 16) for communication and motor drive cables (17, 18) for motor drive, wherein the motor drive cables (17, 18) each comprise a wire (27), a wire insulation layer (28) arranged outside the wire (27), a motor drive cable inner shielding layer (26) covering the wire insulation layer (28), an outer shielding layer (25) arranged outside the motor drive cable inner shielding layer (26) and an outer insulation layer (24) arranged outside the outer shielding layer (25) from inside to outside in sequence;

the communication cables (15, 16) each comprise a twisted pair (29), a communication cable inner shielding layer (41) arranged outside the twisted pair (29), an outer shielding layer (25) arranged outside the communication cable inner shielding layer (41) and an outer insulation layer (24) arranged outside the outer shielding layer (25) from inside to outside in sequence, wherein each wire (27) of the twisted pair (29) is externally provided with a wire insulation layer (28); and the motor drive cable inner shielding layer (26) is a double shielding layer of metal foil and metal braid wire mesh, the communication cable inner shielding layer (41) is metal foil, and the outer shielding layer (25) of the motor drive cables and the communication cables is metal braid wire mesh.

2. The magnetic resonance compatible robot system according to claim 1, wherein the insulation film (30) is insulating coating covering the outside of the motor (11) and the encoder (12), and the metal shielding layer (32) is a metal shielding film covering the inside of the insulation shell (31).

3. The magnetic resonance compatible robot system according to claim 1, wherein the cables (6) comprise an encoder shielding cable (34) and a motor drive shielding cable (35) located in the robot body (4), and the encoder shielding cable (34) and the motor drive shielding cable (35) are both made by a flexible printed circuit board technology.

4. The magnetic resonance compatible robot system according to claim 3, wherein the encoder shielding cable (34) is connected with the communication cables (15, 16) via an encoder jumper holder (21), and the motor drive shielding cable (35) is connected with the motor drive cables (17, 18) via a motor drive cable jumper holder (22).

5. The magnetic resonance compatible robot system according to claim 4, wherein the motor drive shielding cable (35) is integrated with a harmonic filter (36) on one end of the motor drive cable jumper holder (22) for adjusting electrical performance of the motor (11).

6. The magnetic resonance compatible robot system according to claim 4, wherein the communication cables (15, 16) and the motor drive cables (17, 18) for motor drive are connected to the control cabinet (1) respectively via low pass filters (19, 20), a special grounding body (14) and a shielding wall (7), and the low pass filters (19, 20) are arranged in the shielding wall (7).

7. The magnetic resonance compatible robot system according to claim 6, wherein the outer shielding layers (25) of the motor drive cable and the communication cable, the motor drive cable inner shielding layer (26), the communication cable inner shielding layer (41) and housings of the low pass filters (19, 20) are connected with the special grounding body (14), and the special grounding body (14) is grounded via the shielding wall (7).

8. The magnetic resonance compatible robot system according to claim 1, wherein the control cabinet (1) has an aluminum housing, and the aluminum housing is connected to a protective grounding body (37).

9. The magnetic resonance compatible robot system according to claim 1, wherein the robot system also comprises a driver (13), the driver (13) is used for driving the motor (11), the driver (13) comprises a controller (38) and a linear power amplification circuit, the controller (38) is used for producing drive signals, and the linear power amplification circuit performs linear power amplification of the drive signals.

10. The magnetic resonance compatible robot system according to claim 9, wherein the linear power amplification circuit comprises biasing circuits (39) and amplifying circuits (40), each biasing circuit (39) is used for isolating DC voltage components of each amplifying circuit (40) and providing bias voltage for the amplifying circuit (40), and the amplifying circuit (40) is used for amplifying the drive signals.

* * * * *